United States Patent

Cordi et al.

Patent Number: 5,177,240
Date of Patent: Jan. 5, 1993

[54] O-PHOSPHONO(ALKYL)-N-SULFONYL-PHENYL-ALANINE DERIVATIVES USEFUL AS INTERMEDIATES FOR PREPARATION OF PHOSPHONO-HYDROISOQUINOLINES

[75] Inventors: Alexis A. Cordi, St. Louis; Michael L. Vazquez, Ballwin, both of Mo.

[73] Assignee: G. D. Searle & Co., Chicago, Ill.

[21] Appl. No.: 635,798

[22] Filed: Dec. 31, 1990

Related U.S. Application Data

[63] Continuation of Ser. No. 418,092, Oct. 12, 1989, abandoned, which is a continuation-in-part of Ser. No. 260,839, Oct. 20, 1988, Pat. No. 4,997,821.

[51] Int. Cl.$^5$ .............................. C07F 9/40; C07F 9/38
[52] U.S. Cl. .................................. 558/190; 558/191; 562/9; 562/10; 562/11; 546/23
[58] Field of Search ..................... 558/190, 191; 562/9, 562/10, 11

[56] References Cited

U.S. PATENT DOCUMENTS

| | | | |
|---|---|---|---|
| 4,657,899 | 4/1987 | Rzeszotarski et al. | 558/190 |
| 4,761,405 | 8/1988 | Rzeszotarski et al. | 558/190 |
| 4,902,695 | 2/1990 | Ornstein | 546/23 |
| 4,918,064 | 4/1990 | Cordi | 514/114 |

FOREIGN PATENT DOCUMENTS

| | | |
|---|---|---|
| 203891 | 12/1986 | European Pat. Off. |
| 0318935 | 6/1989 | European Pat. Off. ............ 562/11 |
| 3736016 | 5/1988 | Fed. Rep. of Germany |
| 2198134 | 6/1988 | United Kingdom ............... 558/190 |

OTHER PUBLICATIONS

Greene, T. W. Protective Groups in Organic Synthesis; John Wiley and Sons: New York, 1981; pp. 284-287.
S. M. Rothman et al, *Annals of Neurology*, vol. 19, No. 2, 105-111 (1986).
M. N. Perkins et al, *Neuroscience Lett.*, 23, 333-336 (1981).
J. Davies et al, *Neuroscience Lett.*, 21, 77-81 (1981).
K. Matoba et al, *Chem. Pharm. Bull.*, 32 (10)3918-3925 (1984).
J. W. Olney et al, *Neuroscience Letters*, 68, 29-34 (1986).

*Primary Examiner*—Mary C. Lee
*Assistant Examiner*—Michael G. Ambrose
*Attorney, Agent, or Firm*—J. Timothy Keane; Charles E. Smith; Paul D. Matukaitis

[57] ABSTRACT

A class of phosphono-hydroisoquinoline compounds is described for treatment to reduce neurotoxic injury associated with anoxia or ischemia which typically follows stroke, cardiac arrest or perinatal asphyxia. The treatment includes administration of a phosphono-hydroisoquinoline compound alone or in a composition in an amount effective as an antagonist to inhibit excitotoxic actions at major neuronal excitatory amino acid receptor sites. Compounds of most interest are those of Formula I:

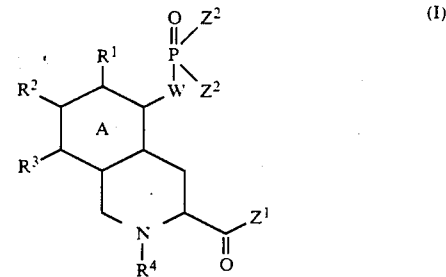

wherein each of $R^1$ through $R^4$ is hydrido, wherein each of $Z^1$ and $Z^2$ is hydroxyl, wherein W is a single bond connecting the phosphorus atom with the aromatic ring and wherein the A ring is aromatic. Also disclosed are two classes of intermediate compounds having a fully unsaturated A ring, which intermediate compounds are useful in methods to make product compounds of Formula I.

7 Claims, No Drawings

O-PHOSPHONO(ALKYL)-N-SULFONYL-PHENYL-ALANINE DERIVATIVES USEFUL AS INTERMEDIATES FOR PREPARATION OF PHOSPHONO-HYDROISOQUINOLINES

This is a continuation of application Ser. No. 418,092 filed Oct. 12, 1989, abandoned, which is a continuation-in-part of application Ser. No. 260,839, filed Oct. 20, 1988 now U.S. Pat. No. 4,997,821.

FIELD OF THE INVENTION

This invention is in the field of clinical neurology and relates specifically to a class of compounds, compositions and methods for neuro-protective purposes such as controlling chronic or acute neurotoxic injury or brain damage resulting from neuro-degenerative diseases. For example, these compounds are particularly useful for treating neurotoxic injury which follows periods of anoxia or ischemia associated with stroke, cardiac arrest or perinatal asphyxia. The compounds would also be useful as anti-convulsants and analgesics.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by specific antagonism of postsynaptic glutamate receptors [see S. M. Rothman and J. W. Olney, "Glutamate and the Pathophysiology of Hypoxia—Ischemic Brain Damage", *Annals of Neuroloqy*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS). Glutamate is believed to be a mixed agonist capable of binding to and exciting all three receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia.

Aminophosphonic acids have been investigated as neurotransmitter blockers [see M. N. Perkins et al, *Neuroscience Lett.*, 23, 333 (1981); and J. Davies et al, *Neuroscience Lett.*, 21, 77 (1981)]. In particular, compounds such as 2-amino-4-(2-phosphonomethylphenyl)-butyric acid and 2-(2-amino-2-carboxy)ethylphenylphosphonic acid have been synthesized for evaluation as antagonists in blocking the action of the neurotransmitter compounds L-glutamic acid and L-aspartic acid [K. Matoba et al, "Structural Modification of Bioactive Compounds II. Syntheses of Aminophosphonic Acids", *Chem. Pharm. Bull.*, 32, (10) 3918–3925 (1984)].

U.S. Pat. No. 4,657,899 to Rzeszotarski et al describes a class of ω-[2-(phosphonoalkylenyl)phenyl]-2-aminoalkanoic acids characterized as being selective excitatory amino acid neurotransmitter receptor blockers. These compounds are mentioned for use as anticonvulsants, antiepileptics, analgesics and cognition enhancers. Typical compounds of the class include 3-[2-phosphonomethylphenyl]-2-aminopropanoic acid and 3-[2-(2-phosphonoethyl)phenyl]-2-aminopropanoic acid. European Patent Application 203,891 of Hutchison et al. describes phosphonoalkyl substituted pipecolic acid derivatives useful for treatment of nervous system disorders in mammals and as antagonists of the NMDA sensitive excitatory amino acid receptor, an example of which is cis-4-phosphonomethyl-2-piperidine carboxylic acid. West German Patent Application 3,736,016 of Sandoz describes phosphonoalkyl phenylglycines derivatives useful as anticonvulsant and as antagonists of the NMDA receptor, an example of which is 3-(phosphonomethyl)phenylglycine. U.S. application Ser. No. 111,749 filed Oct. 21, 1987 describes certain phosphonoalkylphenylglycine derivatives useful in reducing neurotoxic injury and as anticonvulsants and analgesics, an example of which is 4-(phosphonomethyl)phenylglycine.

Other classes of compounds have been tested as agonists in blocking NMDA- or KA-induced neurotoxicity [J. W. Olney et al., "The Anti-Excitotoxic Effects of Certain Anesthetics, Analgesics and Sedative-Hypnotics", *Neuroscience Letters*, 68, 29-34 (1986)]. The tested compounds included phencylidine, ketamine, cyclazocine, kynurenate and various barbiturates such as secobarbital, amobarbital and pentobarbital.

DESCRIPTION OF THE INVENTION

Control of neuropathological processes and the neurodegenerative consequences thereof in mammals is provided by treating a mammal susceptible to neurologic injury with a compound of a class characterized in having activity as antagonists at a major neuronal excitatory amino acid receptor site. This class of NMDA antagonist compounds is also expected to contain compounds having anti-convulsant and analgesic activity. Such NMDA antagonist compounds may be selected from a class of phosphono-hydroisoquinoline compounds defined by Formula I:

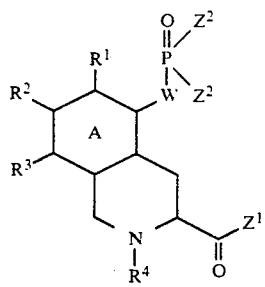 (I)

wherein each of $R^1$ through $R^2$ is independently selected from hydrido, alkyl, haloalkyl, halo, cyano, nitro and groups represented by —$OR^5$, —$SR^5$,

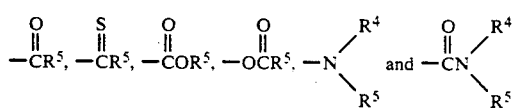

wherein $R^5$ is selected from hydrido, alkyl, aryl and aralkyl; and wherein $R^4$ is selected from hydrido, alkyl, acyl, aralkyl and

and wherein each of $Z^1$ and $Z^2$ is independently selected from —$OR^5$, $SR^5$,

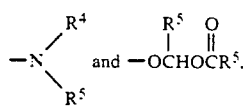

wherein $R^5$ is defined as before; wherein W is a direct bond between the A ring and the phosphorus atom of Formula I, or W is selected from

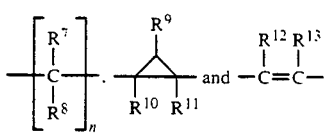

wherein each of $R^7$ through $R^{11}$ is independently selected from hydrido, lower alkyl, cyano, hydroxy, alkoxy, halo and cycloalkyl; wherein n is a number selected from zero, one and two; wherein $R^7$ and $R^8$ may be taken together to form oxo, with the proviso that when n is two, then only one oxo group may be formed; wherein each of $R^{12}$ and $R^{13}$ is independently selected from hydrido, lower alkyl, alkoxy, halo and cycloalkyl; and wherein the A ring can be saturated, or partially unsaturated or fully unsaturated, i.e., an aromatic ring.

Within this class of phosphono-hydroisoquinolines of the invention are the pharmaceutically acceptable salts of the compounds of Formula I, including acid addition salts, base addition salts such as alkali metal salts. Also included within this class of compounds of the invention are tautomeric forms of the defined compounds and isomeric forms including diastereoisomers and enantiomers.

A preferred class of compounds within Formula I consists of those compounds wherein each of $R^1$ to $R^3$ is independently selected from hydrido, alkyl, haloalkyl, halo, cyano, nitro, —$OR^5$ and —$SR^5$; wherein $R^5$ is selected from hydrido, alkyl, aryl and aralkyl; and wherein $R^4$ is selected from hydrido, alkyl, acyl, aralkyl and —$COOR^5$; wherein each of $Z^1$ and $Z^2$ is independently selected from —$OR^5$, —$SR^5$, $NR^4R^5$ and —$OCHR^5OCOR^5$; wherein W is a direct bond between the A ring and the phosphorus atom of Formula I, or W is selected from

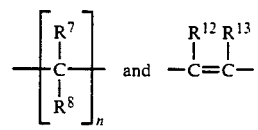

wherein each of $R^7$ and $R^8$ is independently selected from hydrido and lower alkyl; wherein each of $R^{12}$ and $R^{13}$ is independently selected from hydrido and lower alkyl; wherein n is a number selected from zero, one and two; and wherein the A ring can be saturated, or partially unsaturated or fully unsaturated (aromatic).

A more preferred class of compounds within Formula I consists of those compounds wherein each of $R^1$ to $R^3$ is independently selected from hydrido, alkyl, haloalkyl, halo, cyano, —$OR^5$, wherein $R^5$ is selected from hydrido and alkyl; wherein $R^4$ is selected from hydrido, alkyl, acyl, aralkyl and —$COOR^5$; wherein each of $Z^1$ and $Z^2$ is independently selected from —$OR^5$, $NR^4R^5$ and —$OCHR^5OCOR^5$; wherein W is a direct bond between the A ring and the phosphorus atom Formula I, or W is selected from

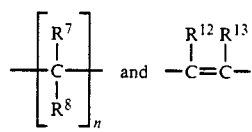

wherein each of $R^7$, $R^8$, $R^{12}$ and $R^{13}$ is hydrido; wherein n is a number selected from zero, one and two; and wherein the A ring can be saturated, or partially unsaturated or fully unsaturated (aromatic).

An even more preferred class of compounds within Formula I consists of those compounds wherein each of $R^1$, $R^2$ and $R^3$ is independently selected from hydrido, halo and alkyl; wherein $R^4$ is selected from hydrido, alkyl, acyl, aralkyl and —$COOR^5$; wherein $R^5$ is selected from hydrido and alkyl; wherein each of $Z^1$ and $Z^2$ is independently selected from —$OR^5$, $NR^4R^5$ and —$OCHR^5OCOR^5$; and wherein the A ring can be saturated, or partially unsaturated or fully unsaturated (aromatic).

A more highly preferred class of compounds within Formula I consists of those compounds wherein each of $R^1$, $R^2$ and $R^3$ is independently selected from hydrido, halo and alkyl; wherein $R^4$ is selected from hydrido, acyl and —$COOR^5$; wherein $R^5$ is selected from hydrido and alkyl; wherein $Z^1$ is selected from —$OR^5$, $NR^4R^5$ and —$OCHR^5OCOR^5$; wherein $Z^2$ is hydroxyl or alkoxy; and wherein the A ring is fully unsaturated (aromatic).

A still more highly preferred class of compounds within Formula I consists of those compounds wherein each of $R^1$, $R^2$, $R^3$, $R^4$ and $R^5$ is independently selected from hydrido, halo and alkyl; wherein each of $Z^1$ and $Z^2$ is independently selected from hydroxyl and alkoxy; wherein W is a direct bond between the A ring and the phosphorus atom of Formula I, and wherein the A ring is fully unsaturated (aromatic).

A most highly preferred class of compounds within Formula I consists of those compounds wherein each of $R^1$, $R^2$, $R^3$, $R^4$ and $R^5$ is independently selected from hydrido, halo and alkyl; wherein each of $Z^1$ and $Z^2$ is independently selected from hydroxyl and alkoxy; wherein W is a direct bond between the A ring and the phosphorus atom of Formula I, and wherein the A ring is fully unsaturated (aromatic). Examples of specific, most highly preferred compounds within this highly preferred class of Formula I are 3-carboxy-5-phosphono-1,2,3,4-tetrahydroisoquinoline, (+)-3-carboxy-5-phosphono-1,2,3,4-tetrahydroisoquinoline, 5-phosphono-3-(ethoxycarbonyl)-1,2,3,4-tetrahydroisoquinoline, and 3-carboxy-5-phosphono-6-methyl-1,2,3,4-tetrahydroisoquinoline.

A second most highly preferred class of compounds within Formula I consists of those compounds wherein each of $R^1$, $R^2$, $R^3$, $R^4$ and $R^5$ is independently selected from hydrido and alkyl; wherein each of $Z^1$ and $Z^2$ is independently selected from hydroxy and alkoxy; and wherein the A ring is partially unsaturated. Examples of specific, most highly preferred compounds within this second highly preferred class of Formula I are 3-carboxy-5-phosphono-1,2,3,4,5,8-hexahydroisoquinoline and 3-carboxy-5-phosphono-1,2,3,4,5,6,7,8-octahydroisoquinoline.

A third most highly preferred class of compounds within Formula I consists of those compounds wherein each of $R^1$, $R^2$, $R^3$, $R^4$ and $R^5$ is independently selected from hydrido and alkyl; wherein each of $Z^1$ and $Z^2$ is independently selected from hydroxy and alkoxy; and wherein the A ring is saturated. An example of a specific, most highly preferred compound within this third highly preferred class of Formula I is 3-carboxy-5-phosphono-2-azadecalin.

All of these specifically-mentioned compounds may exist as racemic mixtures, as dextro-isomers and as levo-isomers. Also, these compounds may be in the form of salts, including alkali metal salts such as the sodium salt.

The term "hydrido" denotes a single hydrogen atom (H) which may be attached, for example, to a carbon atom or to an oxygen atom to form an hydroxyl group. Where the term "alkyl" is used, either alone or within other terms such as "haloalkyl", "aralkyl" and "hydroxyalkyl", the term "alkyl" embraces linear or branched radicals having one to about ten carbon atoms. Preferred alkyl radicals are "lower alkyl" radicals having one to about five carbon atoms. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as bromochloromethyl group. Examples of a polyhaloalkyl are trifluoromethyl, 2,2,2-trifluoroethyl, perfluoroethyl and 2,2,3,3-tetrafluoropropyl groups. The term "alkylthio", as represented by the fragment —$SR^5$, embraces radicals having a linear or branched alkyl portion of one to about ten carbon atoms attached to a divalent sulfur atom, such as a methylthio group. The term "alkoxy", as represented by the fragment —$OR^5$, embraces radicals having a linear or branched alkyl portion of one to about ten carbon atoms attached to an oxygen atom, such as a methoxy group. The term "aryl" embraces aromatic radicals such as phenyl and naphthyl. The term "aralkyl" embraces aryl-substituted alkyl radicals such as benzyl, diphenylmethyl and triphenylmethyl. The terms "benzyl" and "phenylmethyl" are interchangeable. The term "monocycloalkyl" embraces carbocyclic rings of three to about nine carbon atoms, any one of which ring atoms may be further substituted in the manner described herein. Examples of "monocycloalkyl" are cyclopropyl, cyclopentyl and cycloheptyl. The term "polycycloalkyl" embraces two or more monocycloalkyl groups which may be connected together by direct substitution, or by a shared spiro carbon atom, or by bridging two carbons of one of the cycloalkyl rings, or by sharing of two carbon atoms between two fused cycloalkyl rings, or the polycycloalkyl group may be composed of monocycloalkyl rings connected together by any combination of the foregoing bonding arrangements. An example of a "polycycloalkyl" group is camphoryl.

The term "pharmaceuticaly acceptable salts" embraces forms of a salt of addition with a pharmaceutically utilizable acid, either an inorganic acid such as hydrochloric, hydrobromic, hydroiodic, nitric, carbonic, sulfuric or phosphoric acid, or an appropriate organic acid such as an aliphatic, cycloaliphatic, aromatic, araliphatic, heterocyclic, carboxylic or alkylsulfonic acid, specific examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicylic, phenylacetic, mandelic, embonic (pamoic), methanesulfonic, ethanesulfonic, 2-hydroxyethanesulfonic, panthotenic, benzenesulfonic, toluenesulfonic, sulfanilic, mesylic, cyclohexylaminosulfonic, stearic, alginic, $\beta$-hydroxybutyric, malonic, galactaric and galacturonic acid. Also embraced are metallic salts made from aluminium, calcium, lithium, magnesium, potassium, sodium and zinc, and organic salts made from benzathine (N,N'-dibenzylethylenediamine), chloroprocaine, choline, diethanolamine, ethylenediamine, meglumine (N-methylglucamine) and procaine.

The compounds of Formula I can possess one or more asymmetric carbon atoms and are thus capable of existing in the form of different, pure optical isomers as well as in the form of racemic or non-racemic mixtures thereof. All these forms fall within the scope of the present invention. The optical isomers can be obtained by resolution of the racemic mixtures according to conventional processes, for example, by formation of diastereomeric salts by treatment with an optically active acid, such as tartaric, diacetyltartaric, dibenzoyltartaric, ditoluoyltartaric and camphorsulfonic acid, followed by separation of the mixture of diastereomers by crystallization and then followed by liberation of the optically active bases from these salts. Separation of optical isomers may also be achieved by passing the isomer mixture through a chiral chromatography column optimally chosen to maximize the separation of the enantiomers of the products of the invention or derivatives thereof. Still another available method involves synthesis of covalent stereoisomeric molecules by reacting the compounds of the invention with an optically pure acid in an activated form or an optically pure isocyanate. The synthesized diastereoisomers can then be separated by conventional means such as chromatography, distillation, crystallization or sublimation and submitted to an hydrolytic step which will deliver the enantiomerically pure compound. The optically active compounds according to Formula I can likewise be obtained by utilizing optically active starting materials. All of these stereoisomers, optical isomers, diastereomers, as well as mixtures thereof, such as racemic mixtures, are within the scope of the invention.

A therapeutically-active compound of Formula I may be administered alone, or in a solvent, but is more likely to be included in a pharmaceutically-acceptable composition. Such pharmaceutical compositions may contain, as active ingredient, at least one compound of Formula I or its salt of addition with a pharmaceutically utilizable acid, and one or more suitable excipients. These compositions are prepared in such a manner that they can be administered by oral, rectal, parental or local route. The compositions can be solids, liquids or gel forms and may be utilized, according to the administration route, in the form of powders, tablets, lozenges, coated tablets, capsules, granulates, syrups, suspensions, emulsion solutions, suppositories or gels. These compositions can likewise comprise another therapeutic agent having an activity similar to or different from that of the compounds of the invention.

A family of specific compounds of Formula I of particular interest consists of those compounds listed in Table I:

TABLE I 3-carboxy-5-phosphono-1,2,3,4-tetrahydroisoquinoline hydrochloride;
3-carboxy-5-phosphono-1,2,3,4-tetrahydroisoquinoline;
3-carboxy-5-phosphono-1,2,3,4,5,8-hexahydroisoquinoline;
3-carboxy-5-phosphono-1,2,3,4,5,6,7,8-octahydroisoquinoline;
3-carboxy-5-phosphono-6-methyl-1,2,3,4-tetrahydroisoquinoline;
3-carboxy-5-phosphono-7-methyl-1,2,3,4-tetrahydroisoquinoline;
3-carboxy-5-phosphono-8-methyl-1,2,3,4-tetrahydroisoquinoline;
3-carboxy-5-phosphono-6-chloro-1,2,3,4-tetrahydroisoquinoline;
3-carboxy-5-phosphono-7-chloro-1,2,3,4-tetrahydroisoquinoline;
3-carboxy-5-phosphono-8-chloro-1,2,3,4-tetrahydroisoquinoline;
(D)-3-carboxy-5-phosphono-1,2,3,4-tetrahydroisoquinoline;
(L)-3-carboxy-5-phosphono-1,2,3,4-tetrahydroisoquinoline;
5-phosphono-3-(ethoxycarbonyl)-1,2,3,4-tetrahydroisoquinoline;
5-(ethyl phosphono)-3-carboxy-1,2,3,4-tetrahydroisoquinoline;
3-cis-carboxy-5-cis-phosphono-cis-2-azadecalin;
3-cis-carboxy-5-trans-phosphono-cis-2-azadecalin;
3-trans-carboxy-5-trans-phosphono-cis-2-azadecalin;
3-trans-carboxy-5-cis-phosphono-cis-2-azadecalin;
3-cis-carboxy-5-cis-phosphono-trans-2-azadecalin;
3-cis-carboxy-5-trans-phosphono-trans-2-azadecalin;
3-trans-carboxy-5-trans-phosphono-trans-2-azadecalin;
3-trans-carboxy-5-cis-phosphono-trans-2-azadecalin;
3-carboxy-5-(phosphonomethyl)-1,2,3,4-tetrahydroisoquinoline;
3-carboxy-5-(2-phosphonoethyl)-1,2,3,4-tetrahydroisoquinoline; and
3-carboxy-5-(2-phosphonoethenyl)-1,2,3,4-tetrahydroisoquinoline.

SYNTHETIC PROCEDURES

Compounds of Formula I may be prepared in accordance with the following general procedures shown in Schemes I–III which follow:

Scheme I

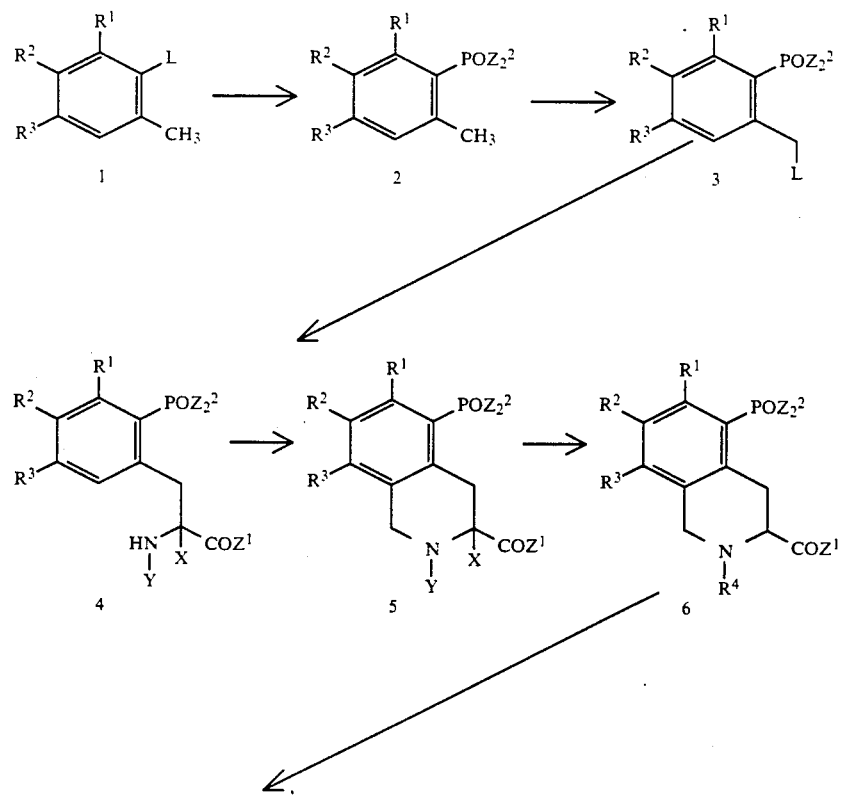

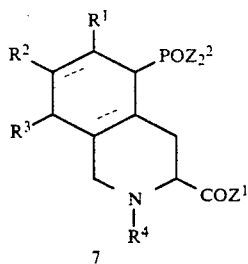

7

One process which can be used to synthesize the products of the invention starts with an ortho toluene derivative of Compound 1 where each of $R^1$, $R^2$ and $R^3$ has the values defined previously and L is a good leaving group such as, for example, halogen, mesylate, tosylate, brosylate and acetate. These ortho toluene derivatives may be treated with dialkylphosphites in the presence of a palladium catalyst or treated first with magnesium in an aprotic anhydrous solvent to form the Grignard reagent which is then reacted further with a chloro dialkylphosphate reagent. The reaction is best achieved by mixing appropriate quantities of the reagents either neat or in a solvent like toluene, tetrahydrofuran, ether or in a protic solvent in the case of the palladium catalyzed reaction, according to the solubility of the reagents, and the reaction temperature can vary from about 0° C. to reflux of the reaction mixture. In the second step of the process, the methyl group of Compound 2 is oxidized to Compound 3. This step is best achieved by treating Compound 2 with an agent able to deliver halogen atoms such as N-bromosuccinimide or N-chlorosuccinimide. The reaction is best conducted in an halogenated solvent such as chloroform, dichloromethane, tetrachloromethane or trichloroethylene at a temperature between 0° C. and reflux temperature of the solvent, with or without irradiation, and in the presence or not of a radical initiator such as azobisisobutyronitrile (AIBN). The leaving group is substituted in the third step with a glycine synthon such as diethylmalonate, acetamidomalonate ($X=COOR^5$, $Y=CH_3CO$), formamidomalonate ($X=COOR^5$, $Y=HCO$), trifluoroacetamidomalonate ($X=COOR^5$, $Y=CF_3CO$), methylsulfonamidomalonate ($X=COOR^5$, $Y=CH_3SO_2$), N-(diphenylmethylene)glycine ethyl ester ($X=H$, $Y=\phi_2C=$) or ethyl isocyanoacetate ($X=H$, $Y=:C=$). Compound 4 obtained from this reaction may require some transformation of the nitrogen substituent Y. For instance, the formamido, acetamido, isocyano and diphenylmethylene residues can be hydrolyzed to the free amine which will be either acylated or sulfonated to provide a compound more suitable for the experimental conditions of the next step.

In the conversion of intermediate 4 to intermediate 5 as shown in Scheme I, it is often desirable to run the conversion reaction under relatively mild conditions and for short reaction periods in order to avoid production of unwanted side-reaction products. Avoidance of unwanted side-reaction products in the conversion of intermediate 4 to intermediate 5 may be accomplished by way of Scheme II.

Scheme II

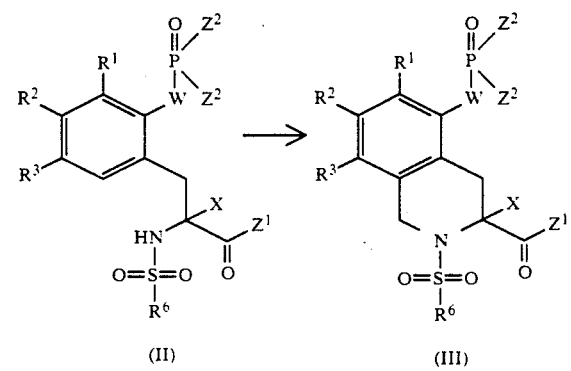

wherein each of $R^1$ through $R^3$ is independently selected from hydrido, alkyl, haloalkyl, halo, cyano, nitro and groups represented by $-OR^5$, $-SR^5$,

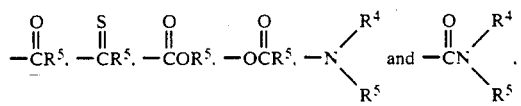

wherein $R^5$ is selected from hydrido, alkyl, aryl and aralkyl; and wherein $R^6$ is selected from alkyl acyl, alkenyl, aryl, aralkyl, monocycloalkyl and polycycloalkyl, and wherein any one of the $R^6$ substituents having a substitutable position may be substituted by one or more groups selected from alkyl, halo, haloalkyl, alkoxy, hydroxy, carboxy, amino, monoalkylamino, dialkylamino, cyano, oxo and

and wherein each of $Z^1$ and $Z^2$ is independently selected from $-OR^5$, $SR^5$,

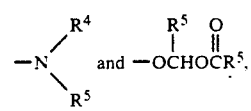

wherein $R^5$ is defined as before; and wherein W is a direct bond between the benzene ring and the phosphorus atom of Formula I, or W is selected from

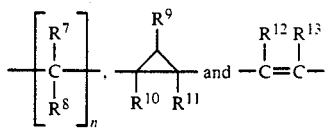

wherein each of $R^7$ through $R^{11}$ is independently selected from hydrido, lower alkyl, cyano, hydroxy, alkoxy, halo and cycloalkyl; wherein n is a number selected from zero, one and two; wherein $R^7$ and $R^8$ may be taken together to form oxo, with the proviso that when n is two, then only one oxo group may be formed; wherein each of $R^{12}$ and $R^{13}$ is independently selected from hydrido, lower alkyl, alkoxy, halo and cycloalkyl.

A preferred class of intermediates within each of Formula II and Formula III consists of compounds wherein each of $R^1$, $R^2$ and $R^3$ is independently selected from hydrido, alkyl, haloalkyl, halo, cyano, nitro, $-OR^5$ and $-SR^5$. More preferred are compounds wherein each of $R^1$ to $R^3$ is independently selected from hydrido, alkyl, haloalkyl, halo, cyano and $-OR^5$, wherein $R^5$ is selected from hydrido and alkyl; and wherein each of $Z^1$ and $Z^2$ is independently selected from $-OR^5$, $NR^4R^5$ and $-OCHR^5OCOR^5$. Still more preferred are compounds wherein each of $R^1$, $R^2$ and $R^3$ is hydrido; wherein $R^6$ is selected from aryl, aralkyl and polycycloalkyl, and wherein any one of the $R^6$ substituents having a substitutable position may be substituted by one or more groups selected from alkyl, halo, haloalkyl, alkoxy, hydroxy, carboxy, amino, monoalkylamino, dialkylamino, cyano, oxo and

wherein $R^5$ is selected from hydrido and alkyl. Highly preferred classes of intermediates within Formula II and Formula III, respectively, consist of compounds wherein $R^5$ is selected from hydrido and alkyl; wherein $R^6$ is selected from phenyl, alkylphenyl and camphoryl; and wherein each of $Z^1$ and $Z^2$ is independently selected from hydroxy and alkoxy. More highly preferred are intermediates wherein each of $R^1$, $R^2$, $R^3$ and $R^5$ is hydrido; and wherein each of $Z^1$ and $Z^2$ is independently selected from hydroxy and alkoxy.

A particularly preferred sulfonamide intermediate of Formula II is ethyl o-(diethylphosphono)phenylalanine-(+)-10-camphorsulfonamide.

A particularly preferred cyclized sulfonamide intermediate of Formula III is ethyl 3-carboxy-5-(diethylphosphono)-N-(+)-10-camphorsulfonamide-1,2,3,4-tetrahydroisoquinoline.

In Scheme II, there is depicted conversion of a sulfonamide compound intermediate of Formula II to a cyclized sulfonamide intermediate of Formula III which sulfonamide compound intermediates are within the scope of intermediates 4 and 5 of Scheme I. As shown in Scheme III, an additional chiral center may be introduced into the Formula II sulfonamide compound by reaction of an intermediate 4 type-compound, wherein Y is hydrido, with a chiral sulfonyl chloride derivative. The resulting Formula II sulfonamide compound may then be cyclized to a Formula III sulfonamide compound with conservation of such chiral center during cyclization and subsequent conversion steps shown in Scheme I. When the sulfonyl chloride derivative possesses a chiral center and is optically pure, there are two possible diastereoisomers which may be formed and which can be easily resolved by chromatography or by fractional crystallization.

The family of compounds of the uncyclized sulfonamide of Formula II and the family of cyclized sulfonamide of Formula III are useful to make the neuroprotective product compounds of Formula I. Both families of compounds of Formula II and Formula III are believed to be novel with the substituent definitions as shown under the Scheme II conversion.

If diethylmalonate has been used as the glycine synthon, it may be necessary to conduct a mono hydrolysis of the diester by stirring the compound in the presence of one equivalent of an alkali hydroxide such as lithium, sodium or potassium hydroxide at room temperature. The acid is carefully transformed into the azido acid either by the mixed anhydride method or by the use of a specific reagent such as diphenylphosphoryl azide. The azido acid is transformed into the amine by thermolysis in an aprotic solvent such as toluene and quenching of the isocyanate formed with dilute HCl.

The cyclization may be conducted by stirring compound 4 in the presence of paraformaldehyde or trioxane and a strong acid such as methanesulfonic acid, trifluoroacetic acid and $BF_3$-etherate in a chlorinated solvent such as 1,2-dichloroethane, or glacial acetic acid. When $R^4$ is equal to acyl or alkoxycarbonyl, complete hydrolysis of $Z^1$, $Z^2$ and $R^4$ can be achieved by an aqueous acid solution, such as 6N HCl or other mineral acid solution. Selective hydrolysis of $R^4$ can be achieved in an acidic alcoholic solution. Selective cleavage of $Z^1$ and $Z^2$ can be achieved by catalytic hydrogenation when $Z^1$ or $Z^2$ is benzyloxy. Various selective deprotection schemes are possible depending on the nature of $R^4$, $Z^1$ and $Z^2$. When $R^1$, $R^2$ or $R^3$ is hydrolyzable, the preferred method of deprotection is by catalytic hydrogenation of hydrogenolytically labile groups. Also, in certain cases deprotection can be effected by use of trimethylsilyl iodide or bromide as the deprotecting agent.

The perhydroisoquinolines can be prepared by the catalytic hydrogenation of the fully or partially deprotected tetrahydroisoquinolines 5 using various metal catalysts such as Pd, Pt, Ni, Ru and Rh. Partially hydrogenated material can be prepared by selective reduction methods, such as the Birch reduction, to obtain dienes followed by selective catalytic hydrogenation to obtain the mono-unsaturated products or the fully saturated compound. The advantage in using different methods of reduction is that different isomers could be obtained among the different racemic mixtures theoretically available.

The following Examples 1-15 are detailed descriptions of the methods of preparation of compounds of Formula I. These detailed preparations fall within the scope of, and serve to exemplify, the above described general procedures which form part of the invention. These Examples are presented for illustrative purposes only and are not intended as a restriction on the scope of the invention. All parts are by weight unless otherwise indicated. Most of the commercially-available starting materials were obtained from Aldrich Chemical Co., Milwaukee, Wis.

EXAMPLE 1

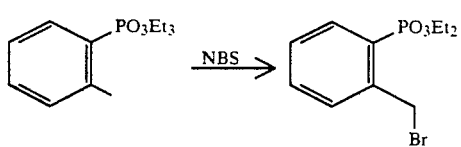

Diethyl 2-methylphenylphosphonate (6.84 gm) and N-bromosuccinimide (NBS) (5.87 gm) were combined in CCl₄ (60 mL). A small amount of azo-bisisobutyronitrile was added and the mixture was heated to reflux. After 6 hours, the NBS had been completely consumed and the orange colored reaction mixture had become a pale yellow. The reaction mixture was cooled to room temperature and the insoluble succinimide removed by filtration. Removal of the solvent on a rotary evaporator afforded a yellow oil. The oil was chromatographed on silica gel (125 gm) eluting with ethyl acetate. The appropriate fractions were pooled and concentrated to afford the product as a colorless oil. Sodium (82 mg) was dissolved in anhydrous ethanol (6 ml) under a nitrogen atmosphere. Diethyl formamidomalonate (725 mg) was then added with stirring. The reaction mixture became homogeneous and then a precipitate began to form. The reaction mixture was briefly heated to reflux and then allowed to cool. The 2-(diethylphosphono)-benzyl bromide (1 gm) was then added and the reaction allowed to stir at room temperature for 20 hours. The reaction mixture was partitioned between H₂O (30 ml) and Et₂O (30 ml). The lower aqueous layer was extracted with fresh Et₂O (30 ml) and the combined Et₂O layers washed once with saturated NaCl (30 ml). The Et₂O layer was then dried (MgSO₄) and concentrated to an oil. The oil was chromatographed on silica gel using ethyl acetate as the eluting solvent. The appropriate fractions were pooled and concentrated to afford the product as a clear oil. Diethyl 2-(2-(diethylphosphono)benzyl)formamidomalonate (430 mg) was combined with paraformaldehyde (31 mg) and acetic anhydride (94 μl) in 1,2-dichloroethane (3.6 ml) containing methanesulfonic acid (0.4 ml) and allowed to stir at room temperature for 7 days. The reaction mixture was diluted with Et₂O (25 ml) and extracted with H₂O (10 ml). The H₂O layer was extracted with Et₂O (25 ml) and the combined Et₂O layers dried (MgSO₄) and concentrated to an oil. The oil was chromatographed on silica gel (50 gm) equilibrated with CH₂Cl₂. The column was eluted with CH₂Cl₂ (100 ml), 1% EtOH/CH₂Cl₂ (200 ml), and then the eluent was held at 2% EtOH/CH₂Cl₂. Fractions of about 10 ml were collected. A few minor impurities eluted followed by the product in fractions 71–79 and unreacted starting material in fractions 82–92. The appropriate fractions were pooled and concentrated to an oil.

EXAMPLE 2

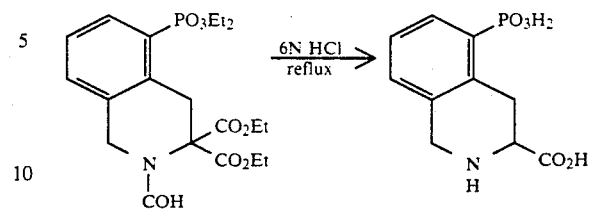

N-Formyl-3-bis(ethoxycarbonyl)-5-(diethylphosphono)-1,2,3,4-tetrahydroisoquinoline (100 mg) was combined with 6N HCl (20 ml) and heated to reflux for 18 hours. The solvent was removed on a rotary evaporator and the resulting white solid dissolved in H₂O (20 ml) and reconcentrated. This process was repeated with ethanol and the final product dried in vacuo.

|   | Elemental Analysis: | |
|---|---|---|
|   | Theory + H₂O | Found |
| C | 38.54 | 38.10 |
| H | 4.85 | 4.90 |
| N | 4.49 | 4.34 |

$^1$H NMR (D₂O) δ* 3.38 (m,1H), 3.78 (m,1H), 4.40 (t,1H), 4.44 (m,2H), 7.36 (m,2H), 7.75 (m,1H).
* relative to HOD peak at 4.72 ppm.

EXAMPLE 2-A

The product compound of Example 2 can also be prepared by replacing the formyl group of diethyl 2-(2-(diethylphosphono)benzyl)formamidomalonate with a sulfonamido group. The compound of Example 2 can also be prepared by making a sulfonamide of ethyl o-(diethylphosphono)phenylalanate followed by cyclization using the method described in Example 1. This step is exemplified in Examples 8, 9, 10, and 11.

EXAMPLE 3

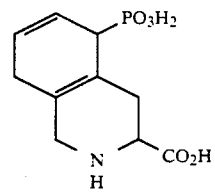

The product compound of Example 2 (0.5 mmol) in anhydrous THF (2 mL) was combined with bis-trimethylsilylacetamide (1.1 mmol) at room temperature. After 15 minutes the reaction became homogeneous and anhydrous ammonia (20 mL) was condensed into the reaction flask using a Dewar condensor (dry ice/isopropanol). A fine white precipitate formed. Sodium metal was added in small pieces until the blue color persisted for 1 hour. The reaction was then quenched with methanol and the ammonia allowed to evaporate. The residue was taken up in water and reconcentrated on a rotary evaporator twice to remove the final traces of ammonia. The residue was then acidified with 1N HCl and concentrated. The resulting solid was triturated with anhydrous ethanol and the ethanol filtered. This step was repeated once. The combined ethanol solutions were concentrated to a white solid. The solid was taken up in a minimal amount of water, filtered, and the clear solution applied to a Dowex 50×8 (H+ form) column (0.5×15 cm). The column was eluted with water until the eluent was neutral and then eluted with 1N pyridine. The ninhydrine positive fractions were pooled and concentrated. The resulting solid was dissolved in a minimal amount of water and precipitated with ethanol. The product was collected by suction filtration, washed with ethanol, then ether, and dried in-vacuo. Mass Spectrometry Data (MS) (M+H)=260, (M-CO₂H)=214 observed; partial ¹H NMR (D₂O) δ*=5.75 (1H, m, vinylic), 5.85 (1H, m, vinylic); collapses to a singlet δ**=5.91 as the free base. [* relative to HOD peak at δ=4.63 ppm.; ** relative to HOD peak at δ=4.79 ppm.]

EXAMPLE 4

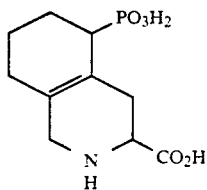

The product compound of Example 3 (0.33 mmol) was suspended in water (2 mL) and 0.5N NaOH (660 uL) was added. To the homogeneous solution was added platinum oxide (3 mg). The reaction flask was evacuated and filled with hydrogen. The hydrogenation was allowed to proceed until one equivalent of hydrogen was consumed. The rate of hydrogen uptake slowed at this point. The catalyst was removed by suction filtration through diatomaceous earth and the resulting solution, contaminated by the catalyst, was concentrated to a solid. The residue was dissolved in water and re-filtered through diatomaceous earth to provide a clear solution. The clear solution was concentrated to a white solid. MS Data (M+H)=262, (M-CO₂H)=216, (M+Na)=284.

EXAMPLE 5

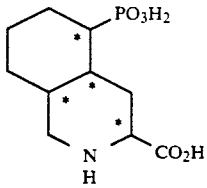

The product compound of Example 3 (0.1 mmol) and platinum oxide (2.5 mg) were suspended in water (2.5 mL). The reaction flask was evacuated and filled with hydrogen. The hydrogenation was allowed to proceed at room temperature until at least 2 equivalents of hydrogen had been consummed. The catalyst was removed by filtration through diatomaceous earth and the resulting clear solution concentrated to a white solid. MS Data (M+H)=264, (M-CO₂H)=218, (M-PO₃H)=184.

EXAMPLE 6

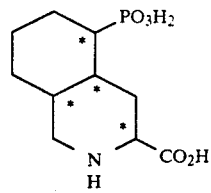

The product compound of Example 2 (0.16 mmol) was suspended in water (10 mL) and 0.5N NaOH (320 uL) was added. To the homogeneous solution was then added 5% rhodium on alumina (40 mg). The reaction flask was filled and flushed 3 times with hydrogen. The mixture was then hydrogenated on a Parr hydrogenator at 50 psi of hydrogen at room temperature for 15 hours. Filtration through diatomaceous earth to remove the catalyst and concentration of the clear solution afforded the product as a white solid. The solid was dissolved in water and applied to a Dowex 50×8 (H+ form) column (0.5×20 cm). The column was eluted with water until the eluent was neutral and then with 1N pyridine. The ninhydrine positive fractions were pooled and concentrated to a solid. The solid was dissolved and reconcentrated from water 3 times to remove final traces of pyridine. The solid was dissolved in water and lyophilized to afford the product. Theory+0.5 H₂O: C, 44.12; H, 7.03; N, 5.15. Found: C, 44.19; H, 6.95, N, 5.31.

EXAMPLE 7

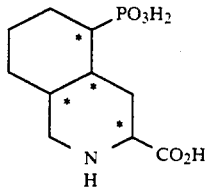

The monosodium salt of the product of Example 2 (0.18 mmol) was dissolved in water (15 mL) and to the homogeneous solution was added platinum oxide (50 mg). The reaction flask was filled and flushed 3 times with hydrogen. The mixture was then hydrogenated on a Parr hydrogenator at 56 psi of hydrogen at room temperature for 72 hours. Filtration through diatomaceous earth to remove the catalyst and concentration of the clear solution afforded the product as a white solid. MS Data (M+H)=264, (M-CO₂H)=218, (M+Na)=286.

EXAMPLE 8

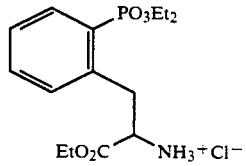

To an anhydrous THF (50 mL), containing HMPA (9 mL), was added a solution of lithium diisopropylamide 1.5M in cyclohexane (18.1 mL). The solution was cooled to −78° C. (dry ice/acetone) and N-(diphenylmethylene)glycine ethyl ester (6.92 gm) in anhydrous THF (25 mL) was added. The dark solution was stirred for 1 hour and then o-(diethyl phosphono)benzyl bromide (7.95 gm) in anhydrous THF (8 mL) was added dropwise over 10 minutes. The reaction was allowed to stir at −78° C. for 1 hour then warm to room temperature with stirring for an additional hour. The solvent was removed on a rotary evaporator and the residue was partitioned between ethyl acetate and water (200 mL each). The layers were separated and the aqueous layer extracted twice with ethyl acetate (100 mL). The combined ethyl acetate layers were washed with water (2×100 mL) and saturated NaCl solution (50 mL), then dried (MgSO$_4$), filtered, and concentrated to a yellow oil. The ethyl o-(diethylphosphono)phenylalanate diphenylmethylene imine (3.25 mmol) was combined with 1N HCl (25 mL) and ethanol (10 mL) and allowed to stir at room temperature for 3 hours. The reaction mixture was then extracted with ethyl acetate (2×30 mL) and the aqueous phase concentrated on a rotary evaporator at 35° C. to a semi-solid. $^1$H NMR CDCl$_3$ δ* 1.31 (3H, t, CH$_3$), 1.34 (3H, t, CH$_3$), 1.40 (3H, t, CH$_3$), 3.60 (2H, d, ArCH$_2$), 4.1–4.4 (7H, m, OCH$_2$ & CH), 7.46 (2H, m, ArH), 7.60 (1H, t, ArH), 7.35 (1H, dd, ArH); δ* relative to TMS set to 0.0 ppm.

EXAMPLE 9

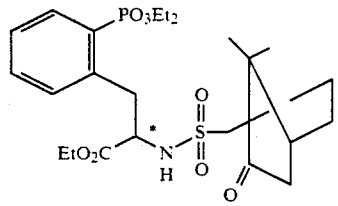

The ethyl o-(diethylphosphono)phenylalanine hydrochloride of Example 8 (3.15 mmol) and (+)-10-camphorsulfonyl chloride (3.45 mmol) were dissolved in dichloromethane (40 mL). Triethylamine (6.9 mL) was added dropwise to the solution. After 3 hours the reaction was diluted with dichloromethane (20 mL) and extracted with water (2×20 mL) and saturated NaCl solution (20 mL). The organic solution was dried (MgSO$_4$), filtered and concentrated to a yellow oil. The oil was chromatographed on silica (125 gm) using 2.5% EtOH/CH$_2$Cl$_2$. The product was isolated as a colorless oil.

EXAMPLE 10

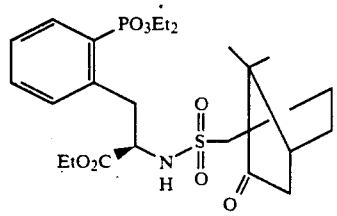

-continued

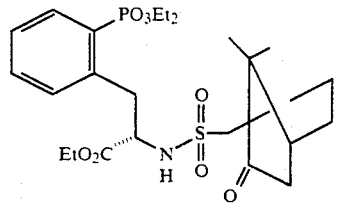

The sulfonamide product of Example 9 was resolved into its diastereoisomers on a preparative HPLC (silica gel 1 Kg) using 1:1 ethyl acetate/hexane as the eluting solvent. The diastereoisomers eluted as a single broad peak (r.i. detector) and were recycled back onto the column. Two distinct peaks were observed after 1 recycle. The various fractions were checked by analytical HPLC using the same conditions. The pure fractions were pooled and concentrated. The compound represented by the first peak formed a solid when concentrated. The compound represented by the second peak remained an oil.

| | | |
|---|---|---|
| Compound 9-A: 1st diastereoisomer | [α]$_{589}$ = | +40.2, |
| | [α]$_{365}$ = | +185.9 (solid) |
| Compound 9-B: 2nd diastereoisomer | [α]$_{589}$ = | −3.2, |
| | [α]$_{365}$ = | +48.2 (oil) |

EXAMPLE 11

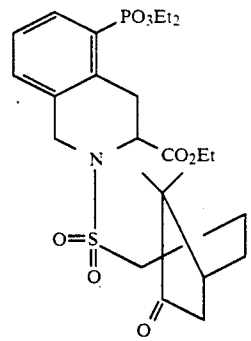

Ethyl o-(diethyl phosphono)phenylalanine-(+)-10-camphorsulfonamide (7.6 mmol) [Compound 9-A; 1st diastereoisomer] and paraformaldehyde (8.0 mmol) were dissolved in a solution of 1,2-dichloroethane (27.5 mL), methanesulfonic acid (3 mL) and acetic anhydride (0.72 mL). The reaction was warmed to 50° C. for 4 hours. The reaction appeared incomplete so an additional 10% paraformaldehyde was added. After an additonal 2 hours the reaction mixture was diluted with dichloromethane (75 mL), extracted with water (3×50 mL), saturated NaCl solution (25 mL), and dried (MgSO$_4$). Filtration and concentration produced an oil. [α]$_{589}$ = −2.0, [α]$_{365}$ = +54.3. partial $^1$H NMR (CDCl$_3$) δ0.75 (3H, s, CH$_3$), 1.01 (3H, s, CH$_3$).

EXAMPLE 12

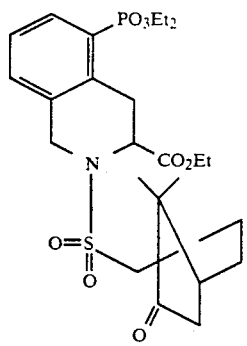

The Compound 9B second diastereoisomer was cyclized in the same fashion as the Compound 9A 1st diastereoisomer described in Example 11, above. $[\alpha]_{589} = +25.5$, $[\alpha]_{365} = +116.6$. partial $^1$H NMR (CDCl$_3$) δ0.78 (3H, s, CH$_3$), 0.96 (3H, s, CH$_3$).

EXAMPLE 13

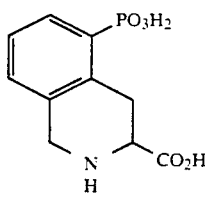

The product of Example 11 (0.3 mmol) was suspended in a solution of concentrated HCl (10 mL), water (5 mL) and ethanol (5 mL). The reaction was heated to reflux for 24 hours and the ethanol allowed to boil off. Additional 6N HCl (20 mL) was added and the reaction mixture was heated at reflux for 48 hours. The solvent was removed on a rotary evaporator. The resulting oil was reconcentrated once from water and once from ethanol to remove final traces of HCl. The oil was taken up in water and a little ethanol was added to clarify the solution. The solution was applied to a Dowex 50×8 (H+ form) column (1×25 cm) and the column eluted with water until the eluent was neutral. The column was then eluted with 1N pyridine. The pyridine eluent was concentrated to a white solid. The solid was dissolved in water and reconcentrated once to remove final traces of pyridine. The solid was then triturated with anhydrous ethanol, collected by suction filtration and washed with ether. $[\alpha]_{365} = +179$ $^1$H NMR is identical to the racemic material. FAB$^-$ MS (M$^-$)=256, (M$^-$-CO$_2$H)=210, (M$^-$-H$_2$O)=238, (M$^-$+Na)=278. When the (+) isomer is hydrolyzed using TMSBr in chloroform followed by concentrated HBr containing phenol, the resulting product has a larger optical rotation $[\alpha]_{365} = +267$.

EXAMPLE 14

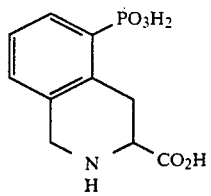

The title compound was prepared by the procedure of Example 13. $[\alpha]_{365} = -180$ $^1$H NMR is identical to the racemic material. FAB$^-$MS (M$^-$)=256, (M$^-$-CO$_2$H)=210, (M$^-$-H$_2$O)=238, (M$^-$+Na)=278.

EXAMPLE 15

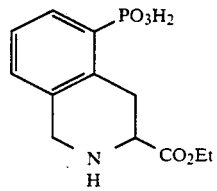

The product compound of Example 2 (0.39 mmol) was dissolved in anhydrous ethanol (20 mL) and this mixture was bubbled with HCl gas. The reaction was then heated to reflux for 9 days. The solvent was removed on a rotary evaporator and the white solid was recrystallized from ethanol/ethyl acetate. Concentration of the mother liquor afforded a residue which was recrystallized from ethanol to afford a second crop. The two crops were combined, dissolved in water and applied to a Dowex 50×8 (H+ form) column (1×30 cm). The column was eluted with water until the eluent was neutral and then eluted with 1N pyridine. The pyridine eluent was concentrated to a white solid.

$^1$H NMR D$_2$O δ* 1.37 (3H, t, CH$_3$), 3.50 (1H, m, ArCH$_2$), 3.97 (1H, m, ArCH$_2$), 4.40 (2H, q, OCH$_2$), 4.52 (1H, m, CH), 4.57 (2H, s, CH$_2$N), 7.41 (2H, m, ArH), 7.85 (1H, m, ArH).

* relative to HOD at 4.80 ppm.

EXAMPLE 16

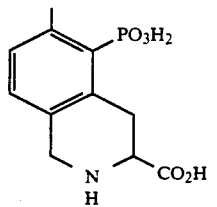

The title compound was prepared in an analogous manner to the procedures used to make the compounds of Examples 14 and 15. The product was isolated as the HCl salt. Theory+0.65 H$_2$O: C, 41.37; H, 5.14; N, 4.38. Found: C, 41.29; H, 4.96; N, 4.38.

EXAMPLE 17

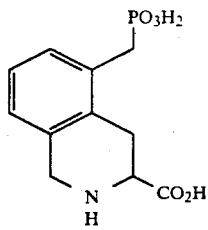

Triethyl phosphite (5.9 mL) and α,α'-dibromo-o-xylene (26.4 gm) were combined with toluene (70 mL) and heated to reflux for 6 hours. The reaction mixture was cooled and then concentrated on a rotary evaporator. The residue was taken up in dichloromethane (50 mL) and chromatographed on silica (350 gm) using dichloromethane until the excess dibromide eluted. The solvent was changed to 5% ethanol/dichloromethane to elute the α-bromo-α'-(diethyl phosphono)-o-xylene. Concentration of the appropriate fractions produced an oil which partially crystallized on standing. Sodium metal (131 mg) was dissolved in anhydrous ethanol (8 mL) and then diethyl formamidomalonate (1.16 gm) was added all at once. The solution quickly became homogeneous and then a precipitate formed. The reaction was briefly heated to reflux and then the α-bromo-α'-(diethyl phosphono)-o-xylene in anhydrous ethanol (2 mL) was added. The reaction was warmed to 45° C. for 24 hours and then the solvent removed on a rotary evaporator. The residue was partitioned between diethyl ether (50 mL) and water (25 mL). The aqueous layer was re-extracted with diethyl ether (50 mL) and the combined ether layers were washed with water (25 mL), dried (MgSO$_4$), and concentrated to an oil. The oil was chromatographed on silica (150 gm) and the column was eluted with dichloromethane (200 mL), 1% ethanol/dichloromethane (200 mL), and then held at 2% ethanol/dichloromethane. As the product eluted it was recycled back onto the column. The product was then collected, concentrated to an oil, and rechromatographed (silica) using ethyl acetate as the eluting solvent. Concentration of the appropriate fractions afforded diethyl formamido-[2-(diethylphosphonomethyl)benzyl]malonate. Diethyl formamido2-(diethyl phosphonomethyl)benzyl]malonate (1 mmol) and paraformaldehyde (1.1 mmol) were dissolved in a solution of 1,2-dichloroethane (3.6 mL), methanesulfonic acid (0.4 mL), and acetic anhydride (1 mmol). The reaction was warmed to 50° C. for 8 hours then allowed to stir at room temperature for 6 days. The reaction mixture was partitioned between water (25 mL) and diethyl ether (50 mL). The aqueous layer was extracted with diethyl ether (25 mL) and the combined ether layers washed with water (20 mL), dried (MgSO$_4$), and concentrated to a semi-solid. The solid was chromatographed on a silica gel column (50 gm). The column was eluted with dichloromethane (100 mL), 1% ethanol/dichloromethane (400 mL), 2% ethanol/dichloromethane (270 mL), then held at 3% ethanol/dichloromethane. Fractions of about 25 mL were collected and the product was eluted in fractions 92-108. The fractions were pooled and concentrated to a solid. The solid was combined with 6N HCl (20 mL) and heated to reflux for 24 hours, then concentrated on a rotary evaporator. The residue was taken up in water and reconcentratred several times to remove final traces of HCl. The material was then applied to a Dowex 50×8 (H$^+$ form) column (1×20 cm) and the column eluted with water (50 mL). The column was then eluted with 1N pyridine (100 mL). The pyridine eluent was concentrated to a white solid. The solid was taken up in water (15 mL), briefly heated to reflux, and filtered to remove insoluble material. The aqueous solution was concentrated to about 5 mL and allowed to cool slowly and stand at room temperature for several days. The resulting crystals were collected by suction filtration, washed with ethanol, diethyl ether, and dried in-vacuo. Elemental Analysis: Theory+1.1 H$_2$O: C, 45.40; H, 5.61; N, 4.81; Found: C, 45.04; H, 5.59; N, 4.69. NMR (D$_2$O/DCl)* d 3.09 (1H, m), 3.12 (2H, d) (overlapping signals), 3.45 (1H, m), 4.29 (1H, dd), 4.34 (2H, s), 7.04 (1H, m), 7.17 (2H, d). * relative to HDO signal at 4.65 ppm.

BIOLOGICAL EVALUATION

NMDA Receptor Binding Assays

Synaptic plasma membranes (SPM) were prepared as previously described Monahan, J. B. and Michel, J., "Identification and Characterization of an N-methyl-D-aspartate-specific L-[$^3$H]-glutamate Recognition Site in Synaptic Plasma Membranes, *J. Neurochem.*, 48, 1699-1708 (1987)]. The SPM were stored at a concentration of 10-15 mg/ml in 0.32M sucrose, 0.5 mM EDTA, 1 mM MgSO$_4$, 5 mM Tris/sulfate, pH 7.4, under liquid nitrogen. The identity and purity of the subcellular fractions were confirmed by both electron microscopy and marker enzymes. Protein concentrations were determined by using a modification of the method of Lowry [Ohnishi, S. T. and Barr, J. K., "A Simplified Method of Quantitating Proteins Using the Biuret and Phenol Reagents", *Anal. Biochem.*, 86, 193-197 (1978)]. The SPM were treated identically for the [$^3$H]AMPA (QUIS), [$^3$H]kainate and sodium-dependent L-[$^3$H]-glumatate binding assays. The SPM were thawed at room temperature, diluted twenty-fold with 50 mM Tris/acetate, pH 7.4, incubated at 37° C. for 30 minutes, and centrifuged at 100,000 g for 15 minutes. The dilution, incubation and centrifugation were repeated a total of three times. Prior to use in the NMDA-specific L-[$^3$H]-glutamate binding assay, the SPM were thawed, diluted twenty fold with 50 mM Tris/acetate (pH 7.4 containing 0.04% (v/v) Triton X-100), incubated for 30 minutes at 37° C. and centrifuged as described above. The Triton X-100 treated membranes were washed with 50 mM Tris/acetate (pH 7.4) and centrifuged at 100,000 g for 15 minutes a total of four times. The basic procedure for the receptor subclass binding assays was similar. This general method involved adding the radioligand (12.5 nM L-[$^3$H]-glutamate; 0.5 nM [$^3$H]kainate or 10nM [$^3$H]AMPA) to the appropriate concentration of the test compound and initiating the assay by the addition of ice cold synaptic plasma membranes (0.2-0.45 mg). The binding assays were performed in 1.5 mL centrifuge tubes with the total volume adjusted to 1.0 mL. Additions of test compounds were made in 50 mM Tris/acetate (pH 7.4) and incubations were carried out at 0°-4° C. The incubation time for each of the NMDA and the AMPA binding assays was 10 minutes, for the kainate binding assay 60 minutes and for the sodium-dependent glutamate binding assay 15 minutes. The AMPA binding assay contained 100 mM KSCN and the sodium-dependent glutamate binding assay contained 150 mM sodium acetate in addition to the previously described reagents. To terminate the incubation, the samples were centrifuged for 15 minutes at 12,000 g and 4° C. in a Beckman Microfuge 12. The supernatant was aspirated and the pelleted membranes dissolved in Beckman BTS-450 tissue solubilizer for a minimum of 6 hours at room temperature. Beckman MP scintillation cocktail containing 7 mL/L acetic acid was then added and the samples counted on a Beckman LS 5800 or 3801 liquid scintillation counter with automatic corrections for quenching and counting efficiency. Nonspecific binding was defined as the residual binding in the presence of either excess L-glutamate (0.1-0.4 mM), kainate (0.01 mM), or NMDA (0.5 mM), and was 15-25% of the total binding in the NMDA binding assay, 19-27% in the AMPA binding assay, 20-30% in the kainate binding assay and 10-15% in the sodium-dependent binding assay. Radioligand binding to the synaptic plasma membranes was analyzed using Scatchard and Hill transformations and the $K_i$ values of the compounds determined using logit-log transformations. Calculations and regression analysis were performed using templates developed for Lotus 1, 2, 3 as previously described [Pullan, L. M. "Automated Radioligand Receptor Binding Analysis with Templates for Lotus", *Computer Appln. Biosci.*, 3 131 (1987)]. Binding results are reported in Table II for example compounds of the invention. Included in Table II are binding data for D,L-AP7[D,L-2-amino-7-phosphonoheptanoic acid].

TABLE II

| NMDA RECEPTOR BINDING | | | |
|---|---|---|---|
| | $K_i(\mu M)$ | | |
| Compound | NMDA | KA | Quis |
| D.L-AP7 | 5.4 | >300 | >300 |
| D-AP7 | 4.0 | >300 | >300 |
| Ex. 2 | 1.6 | ~300 | >300 |
| Ex. 3 | 3.0 | | |
| Ex. 4 | 1.2 | | |
| Ex. 5 | 1.6 | | |
| Ex. 6 | 11.2 | | |
| Ex. 7 | 1.3 | | |
| Ex. 13 | 0.9 | | |
| Ex. 14 | 3.1 | | |
| Ex. 15 | >100.0 | | |
| Ex. 16 | 5.9 | | |
| Ex. 17 | 18.0 | | |

TCP Modulation Assay

The effect on the TCP (1-[1-(2-thienyl)-cyclohexyl]-piperidine) binding was measured in rat brain synaptic membranes (SPM) prepared as previously described [J. B. Monahan & J. Michel; J. Neurochem. 48:1699-1708 (1987)]. Prior to their use in the binding assay, frozen SPM were thawed, diluted twenty fold with 50 mM Tris/acetate (pH 7.4 containing 0.04% (v/v) Triton X-100), incubated for 30 min. at 37° C. and centrifuged at 95,000×g for 15 min. The Triton X-100 treated SPM were washed with 5 mM Tris/HCl, pH 7.4 and centrifuged a total of six times. The compound of Example II was incubated at different concentrations with SPM (0.2-0.4 mg protein) and 2 nM tritiated TCP, in a total volume of 0.5 ml of 5 mM Tris/HCl buffer pH 7.4 at 25° C. for 60 min. The samples were filtered through glass fiber filters (Schleicher & Schuell #32) which have been pretreated with 0.05% (v/v) polyethylenimine, washed 4 times with 2 ml of ice-cold 5 mM Tris/HCl buffer, and then counted on a Beckman LS 5800 liquid scintillation counter with automatic corrections for quenching and counting efficiency. Inhibition of TCP binding was measured as a decrease in the binding in the presence of 0.05 mM L-glutamate. Non-specific binding was defined as the residual binding in the presence of 60 mM phencyclidine.

Result: The compound of Example 2 inhibits 64% of TCP binding at 5 $\mu$M and 91% at 50 $\mu$M.

Glycine Binding Assay

Synaptic plasma membranes (SPM) were prepared from rat forebrain and stored as previously described [J. B. Monahan and J. Michel, *J. Neurochem.*, 48, 1699-1708 (1987)]. Frozen membranes were thawed and diluted 1:20 with 0.04% Triton X-100 in 50 mM Tris/acetate (pH 7.4). Following incubation at 37° C. for 30 min., the SPM were collected by centrifugation at 95,000×g for 15 min. The pellet was resuspended in 50 mM Tris/acetate (pH 7.4, Triton-free) and hand-homogenized five times. The membranes were again centrifuged as above. The pellet was washed two additional times with 50 mM Tris/acetate (without homogenization) and centrifuged. The final pellet was resuspended with homogenization in 50 mM Tris/acetate. In the general receptor binding assay procedure, 10 nM [$^3$H]glycine was added to the appropriate concentration of the test compounds and the assay initiated by the addition of 0.2-0.4 mg of ice cold SPM. The assay, which was done in 1.5 ml centrifuge tubes, was adjusted to a total volume of 1.0 ml with all additions being made in 50 mM Tris/acetate, pH 7.4 at 4° C. After a 10 minute incubation at 2° C., the samples were centrifuged for 15 min. at 12,000 g (4° C.) in a Beckman Microfuge 12. The supernatant was aspirated and the tube tip containing the pelleted membranes cut off and agitated in 0.5 ml of Beckman BTS-450 tissue solubilizer for a minimum of 6 hours at room temperature. Beckman MP scintillation cocktail (5 ml) containing 7 ml/liter acetic acid was then added and the samples counted on a Beckman LS 5800 liquid scintillation counter with automatic corrections for quenching and counting efficiency. Nonspecific binding was defined as the residual binding in the presence of 0.1 mM glycine and usually amounted to 25-35% of the total binding. The binding of [$^3$H]glycine to the SPM was analyzed using Scatchard and Hill transformations and the $K_i$ for other compounds was determined using logit-log analysis. Calculations and regression analysis were performed using templates developed for Lotus 123 as previously described. An $IC_{20}$ value of 1.9 $\mu$M was calculated, based on the maximum inhibition of [$^3$H]-glycine binding induced by the Compound of Ex. 2, as approximately 40%.

MK-801 Modulation Assay

[$^3$H]MK-801 binding was performed using Triton X-100 washed synaptic plasma membranes (SPM) prepared from rat forebrain (30-45 day old, male Sprague-Dawley; Sasco, St. Charles, MO) as described previously [J. W. Thomas, W. F. Hood, J. B. Monahan, P. C. Contreras and T. L. O'Donohue, Brain Res., 442, 396-398 (1988)]. The assay was initiated by the addition of SPM (0.20-0.30 mg) to an incubation containing 2.0 nM [$^3$H]MK-801 (15 Ci/mmole; New England Nuclear, Boston, MA) and various concentrations of the appropriate test compound in a total volume of 0.5 ml (all additions were made in 50mM Tris/acetate buffer, pH 7.4) and continued for 120 min at 25° C. The samples were then filtered through glass fiber filters (Schleicher and Schuell #32) which were pretreated with 0.05% (v/v) polyethylenimine. The filters were washed and the radioactivity quantitated by liquid scintillation spectrometry. Inhibition of [³H]MK-801 binding was measured as a decrease in specific basal binding (basal binding=2583 ±381 DPM) with nonspecific binding as the residual binding in the presence of 60 μM MK-801 (562 ±30 DPM). The $IC_{50}$ values for the inhibition of [³H]MK-801 binding were determined using a logit-log analysis and are reported in Table III, below.

TABLE III

| [³H] MK-801 Receptor Binding | |
|---|---|
| Compound | $IC_{50}$, μM |
| Ex. 2 | 0.48 |
| Ex. 5 | 1.38 |

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

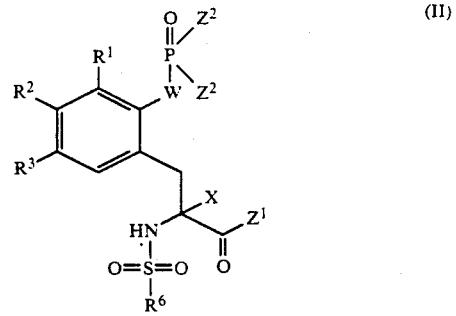

wherein each of $R^1$ through $R^3$ is independently selected from hydrido, alkyl, haloalkyl, halo, cyano, nitro and groups represented by $-OR^5$, $-SR^5$,

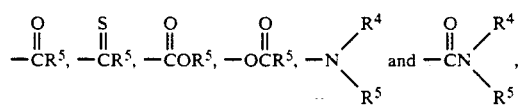

wherein each $R^5$ is independently selected from hydrido, alkyl, aryl and aralkyl; and wherein $R^6$ is selected from alkyl, acyl, alkenyl, aryl, aralkyl, monocycloalkyl and polycycloalkyl, and wherein any one of the $R^6$ substituents having a substitutable position may be substituted by one or more groups selected from alkyl, halo, haloalkyl, alkoxy, hydroxy, carboxy, amino, monoalkylamino, dialkylamino, cyano, oxo and

and wherein each of $Z^1$ and $Z^2$ is independently selected from $-OR^5$, $SR^5$,

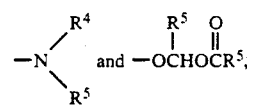

wherein $R^5$ defined as before; wherein W is a direct bond between the benzene ring and the phosphorus atom of Formula II, or W is selected from

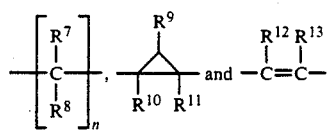

wherein each of $R^7$ through $R^{11}$ is independently selected from hydrido, lower alkyl, cyano, hydroxy, alkoxy, halo and cycloalkyl; wherein n is a number selected from zero, one and two; wherein $R^7$ and $R^8$ may be taken together to form oxo, with the proviso that when n is two, then only one oxo group may be formed;

wherein each of $R^{12}$ and $R^{13}$ is independently selected from hydrido, lower alkyl, alkoxy, halo and cycloalkyl; and wherein X is selected from hydrido and groups represented by

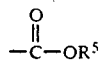

wherein $R^5$ is defined as before.

2. Compound of claim 1 wherein each of $R^1$, $R^2$ and $R^3$ is independently selected from hydrido, alkyl, haloalkyl, halo, cyano, nitro, $-OR^5$ and $-SR^5$; wherein W is a direct bond between the A ring and the phosphorus atom of Formula II, or W is selected from

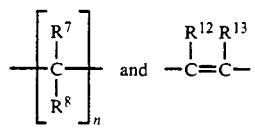

wherein each of $R^7$ and $R^8$ is independently selected from hydrido and lower alkyl; wherein each of $R^{12}$ and $R^{13}$ is independently selected from hydrido and lower alkyl, wherein n is a number selected from zero, one and two.

3. Compound of claim 2 wherein each of $R^1$ to $R^3$ is independently selected from hydrido, alkyl, haloalkyl, halo, cyano and $-OR^5$, wherein $R^5$ is selected from hydrido and alkyl; and wherein each of $Z^1$ and $Z^2$ is independently selected from $-OR^5$, $NR^4R^5$ and $-OCHR^5OCOR^5$; wherein W is a direct bond between the A ring and the phosphorus atom of the Formula II, or W is selected from

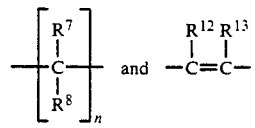

wherein each of $R^7$, $R^8$, $R^{12}$ and $R^{13}$ is hydrido; and wherein n is a number selected from zero, one and two.

4. Compound of claim 3 wherein each of $R^1$, $R^2$ and $R^3$ is hydrido; wherein $R^6$ is selected from aryl, aralkyl and polycycloalkyl, and wherein any one of the $R^6$ substituents having a substitutable position may be substituted by one or more groups selected from alkyl, halo, haloalkyl alkoxy, hydroxy, carboxy, amino, monoalkylamino, dialkylamino, cyano, oxo and

wherein $R^5$ is selected from hydrido and alkyl.

5. Compound of claim 4 wherein $R^5$ is selected from hydrido and alkyl; wherein $R^6$ is selected from phenyl, alkylphenyl and camphoryl; and wherein each of $Z^1$ and $Z^2$ is independently selected from hydroxy and alkoxy.

6. Compound of claim 5 wherein each of $R^1$, $R^2$, $R^3$ and $R^5$ is hydrido; wherein $R^6$ is selected from phenyl, alkylphenyl and camphoryl; and wherein each of $Z^1$ and $Z^2$ is independently selected from hydroxy and alkoxy.

7. Compound of claim 5 which is ethyl o-(diethylphosphono)phenylalanine-(+)-10-camphorsulfonamide.

* * * * *